(12) United States Patent
Paik et al.

(10) Patent No.: US 6,887,852 B1
(45) Date of Patent: May 3, 2005

(54) PHARMACEUTICAL PREPARATION OF RECOMBINANT FACTOR VIII LYOPHILIZED WITHOUT ALBUMIN AS A STABILIZER

(75) Inventors: Sang Hoon Paik, Yongin-si (KR); Yong Nam Shin, Wonju-si (KR); Jean Man Kim, Yongin-si (KR); Jae Wook Huh, Yongin-si (KR); Jung Sik Lee, Yongin-si (KR); Ki Sung Kwon, Gwacheon-si (KR); Ji Hyun Chun, Yongin-si (KR)

(73) Assignee: Korea Green Cross Corporation, Yongin-si (KR)

( * ) Notice: Subject to any disclaimer, the term of this patent is extended or adjusted under 35 U.S.C. 154(b) by 0 days.

(21) Appl. No.: 10/912,167

(22) Filed: Aug. 6, 2004

(30) Foreign Application Priority Data

Jun. 25, 2004 (KR) .................. 10-2004-0047985

(51) Int. Cl.[7] .................. A61K 38/00; A61K 35/14; C12P 21/02
(52) U.S. Cl. .................. 514/12; 530/383; 435/69.6
(58) Field of Search .................. 530/383; 435/69.6; 514/12

(56) References Cited

U.S. PATENT DOCUMENTS 5,407,671 A * 4/1995 Heimburger et al. ...... 424/94.1

FOREIGN PATENT DOCUMENTS

| EP | 0 077 870 A2 | 5/1983 |
| EP | 0 268 110 A1 | 5/1988 |
| WO | WO-89/09614 A1 | 10/1989 |
| WO | WO-91/10439 A1 | 7/1991 |
| WO | WO 93/22336 | * 11/1993 |
| WO | WO 96-/22107 A1 | 7/1996 |
| WO | WO-96/22107 A1 | 7/1996 |

* cited by examiner

*Primary Examiner*—Robert A. Wax
*Assistant Examiner*—Suzanne M. Mayer
(74) *Attorney, Agent, or Firm*—Birch, Stewart, Kolasch & Birch, LLP

(57) ABSTRACT

Disclosed is a lyophilized preparation of recombinant factor VIII used as a therapeutic preparation of hemophilia A. The lyophilized preparation of recombinant factor VIII is prepared by performing lyophilization using a mixture comprising 6 to 100 mM of L-arginine, 3.5 to 50 mM of L-isoleucine, and 10 to 100 mM of L-glutamic acid as a stabilizer for stabilizing the recombinant factor VIII which exhibits an unstable activity during lyophilization, rather than using human blood derived albumin.

8 Claims, 3 Drawing Sheets

Experiment 1
Factor VIII with
albumin

Experiment 2
Factor VIII with a
non-ionic surfactant

Experiment 16
Factor VIII without
albumin

PHARMACEUTICAL PREPARATION OF RECOMBINANT FACTOR VIII LYOPHILIZED WITHOUT ALBUMIN AS A STABILIZER This Non-provisional application claims priority under 35 U.S.C. § 119(a) on Patent Application No(s). 10-2004-0047985 filed in Korea, Republic of on Jun. 25, 2004, the entire contents of which are hereby incorporated by reference.

BACKGROUND OF THE INVENTION

1. Field of the Invention

The present invention relates to a lyophilized composition of recombinant factor VIII used as a therapeutic preparation of hemophilia A, and more particularly, to a lyophilized composition recombinant factor VIII without albumin using an amino acid as a stabilizer for stabilizing the recombinant factor that is unstable in activity during lyophilization, the amino acid being free from a risk of viral infection.

2. Description of the Related Art

Hemophilia is one of inherited coagulation disorders and is known to be caused due to a shortage of biologically active coagulation factors, which are normally present in the blood human blood plasma.

Since hemophilia is an inherited sex-linked recessive bleeding disease, females are very rarely affected even if the females have hemophilia genes, affecting mainly the male population. The hemophilia is classified into hemophilia A, hemophilia B, hemophilia AB and hemophilia C according to the type of deficient blood clotting factor.

Hemophilia A affects 1-2 individuals per 20,000 males due to deficiency or absence of human in vivo blood coagulating factor VIII (antihemofilic factor). Hemophilia B occurs in about 1 of 100,000 males due to deficiency of human blood coagulation factor IX (Christmas factor). Hemophilia AB reflects a deficiency of human recombinant blood coagulating factors VIII and IX, and hemophilia C reflects a deficiency of human recombinant coagulating factor XI.

Therapeutic agents for the treatment of hemophilia A have been produced for the last three decades by isolating the factor VIII from human blood plasma, purifying and concentrating the same. Such therapeutic agents have allowed many hemophiliacs to lead a normal life.

However, the human blood derived coagulating factor VIII, which is isolated from human blood plasma to be used as the conventional therapeutic agents for the treatment of hemophilia, encountered certain disadvantages, including susceptibility to infection with blood-mediated viruses such as hepatitis, human immunodeficiency virus (HIV) or TT virus. To overcome such problems, as reported in J. Gitschier et al., Nature 312, 330–37, 1984 and EP 160 457, preparation of recombinant human coagulating factor VIII generally involves isolating the same from recombinant animal cell culture products using recombinant DNA technology and purifying the isolated coagulating factors.

The structure and biochemical reaction scheme of recombinant factor VIII products are described in Kaufman Tibtech, Vol 9, 1991 and Hematology, 63, 155–65, 1991.

Human factor VIII concentrates isolated from human blood plasma contain several fragmented factor VIII forms of stable activity (see Andersson et al., Proc. Natl. Acad. Sci. USA, Vol 83, 2979–83, May 1986). The smallest active form of factor VIII has a molecular weight of about 170 kDa and is composed of two chains of 90 kDa and 80 kDa fragments linked to each other by metal ion crosslinkage (see EP 197 901). Kabi Pharmacia developed recombinant factor VIII products of 170 kDa with a B-domain deleted from human blood derived coagulating factor VIII. The severed recombinant factor, which is termed r-VIII SQ, and is produced by recombinant Chinese Hamster ovary (CHO) cell line from serum-free media by animal cell cultivation. The structure and biochemical reaction scheme of r-VIII SQ are described in WO 91/09122.

Recombinant factor proteins are produced in a lyophilized form to be commercially distributed for better preservation, storage and handling. For being administered to a patient, the lyophilized proteins are reconstituted in an appropriate solvent. During lyophilization, however, the recombinant factor proteins may experience a considerable reduction in the activity while undergoing purification, sterilization, lyophilization, packaging and reconstitution for injection. Also, dry cake appearance is undesirably poor. Thus, a conventional attempt was made to achieve stabilization of recombinant factor using human blood derived albumin as a stabilizer in lyophilization. The human blood derived albumin serves as a general stabilizer in purification and sterilization as well as lyophilization (see Wang et al., J. of Parenteral Sci. and Tech. Vol 42, Number 2S, Supplement. 1988). Also, the human blood derived albumin is a good cake-forming agent in formulations for lyophilization. The use of albumin in stabilizing recombinant factor VIII is widely known in the art, and albumin is also employed to some products of highly purified recombinant factor VIII that are currently commercially available. However, since the human blood derived albumin is isolated from human blood plasma, it is vulnerable to infection with blood-derived viruses such as hepatitis, HIV, or TT virus. Therefore, the human blood derived albumin cannot be suitably used for hemophilia therapeutic agents produced by recombinant DNA technology. Further, when a physico-chemical test is performed on final products, excess albumin relative to a small concentration of main pharmaceutically effective components may cause interference, making accurate quality control difficult.

Thus, it would be desirable to provide a pharmaceutical preparation of recombinant factor without albumin, which is stable in a solution during lyophilization or as a solution resulting after lyophilization and reconstitution.

To stabilize recombinant factors, various attempts have been proposed. For example, U.S. Pat. No. 5,763,401 (EP 818 204, Bayer) discloses a method of stabilizing recombinant factor using 15 to 60 mM of sucrose as a stabilizer.

U.S. Pat. No. 5,733,873 (EP 627 924, Pharmacia & Upjohn) discloses a stabilization method of a recombinant factor using 0.01 to 1 mg/ml of a non-ionic surfactant (polysorbate 20 or 80) as a stabilizer.

U.S. Pat. No. 4,877,608 (EP 315 968, Rhone-Poulenc Rorer) discloses a stabilization method of a recombinant factor using low concentration ions, that is, 0.5 to 15 mM of NaCl, KCl and 0.01 to 10 mM of lysine hydrochloride, to which sugar such as maltose, sucrose or mannitol may be further added.

U.S. Pat. No. 5,605,884 (EP 314 095, Rhone-Poulenc Rorer) discloses a stabilization method of a recombinant factor using high concentration ions, that is, 0.35 to 1.2 M NaCl, and 1.5 to 40 mM KCl, to which saccharides such as maltose, sucrose or mannitol may also be further added.

International Patent Application WO 96/22107 (Quadrant Holings Cambrige Limited) discloses use of trehalose as a stabilizer.

International Patent Application WO 89/09614 (Genentech) describes a formulation having stabilized human growth hormone including glycine, mannitol and a buffer. In a preferred embodiment of the formulation, a non-ionic surfactant, such as polysorbate 80, is added thereto. The non-ionic surfactant is added for reduced aggregation and denaturation. The prepared formulation exhibits increased stability during lyophilization and after reconstitution.

EP 268 110 (Cetus) describes a solution comprising a particular protein dissolved in an inactive carrier medium containing a non-ionic polymer clarificant as a solvent/stabilizer, for example, interleukin-2. Preferred examples of the clarificant include octylphenoxy polyethoxy ethanol compound, polyethylene glycol monostearate compound and polyethylene sorbitan fatty acid ester.

U.S. Pat. No. 4,783,441 (Hoechst) describes an aqueous solution containing proteins, for example, insulin and a pulmonary surfactant.

U.S. Pat. No. 165,370 (Coval) discloses a gamma globulin solution and a preparation method thereof. The disclosed solution contains polyethylene glycol (PEG). The solution may further include a non-ionic surfactant.

EP 77 870 (Japan Green Cross) discloses adding amino acids, monosaccharides, oligosaccharides, sugar alcohol or hydrocarbon carboxyl acid to a solution containing a recombinant factor in order to improve stability of the solution. EP 117064 describes adding sugar alcohol or disaccharide to an aqueous solution of a recombinant factor in order to increase stability during annealing.

International Patent Application WO 91/10439 (Octopharma) discloses a stable injectable solution of factor VIII or factor IX containing disaccharide, preferably saccharose, and one or more kinds of amino acids.

SUMMARY OF THE INVENTION

The present invention provides a novel pharmaceutical preparation recombinant factor VIII lyophilized without albumin, which exhibits substantially the same pharmaceutical efficacy with an albumin-containing product while capable of preventing viral infection caused by the use of human blood derived albumin as a stabilizer of the conventional recombinant factor.

The pharmaceutical preparation of recombinant factor VIII lyophilized without albumin according to the present invention can be achieved using a mixture of arginine, isoleucine and glutamic acid as a stabilizer.

The pharmaceutical preparation of recombinant factor VIII without albumin according to the present invention is substantially the same with the conventional pharmaceutical preparation of recombinant factor VIII with albumin in view of cake appearance, post-reconstitution activity, and post-reconstitution clarity.

DETAILED DESCRIPTION OF THE INVENTION

Figure 1:
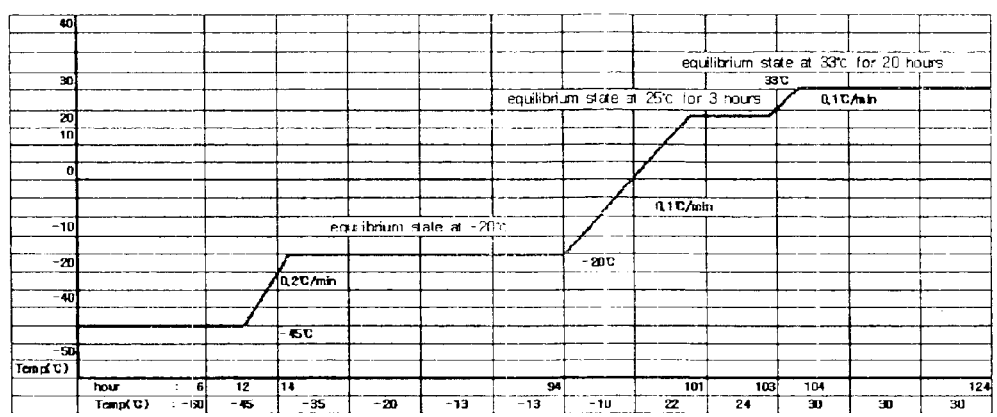
FIG. 1 shows a lyophilization process of pharmaceutical preparation of recombinant factor VIII according to the present invention.

The present invention provides a pharmaceutical preparation of recombinant factor VIII lyophilized without albumin while exhibiting high stability.

In order to discover new stabilizers for lyophilization as substitutes of existing human blood borne albumin, the present inventors carried out lyophilization experiments by adding a mixture of particular amino acids in a predetermined mixing ratio to recombinant factor VIII and found that the resulting recombinant factor VIII has high activity, good cake appearance and clarity even after it is lyophilized.

The present invention will now be described in detail.

The term "recombinant factor VIII concentrate" used in the present invention refers to a solution prepared by purifying a nutrient solution containing recombinant factor VIII obtained by culturing animal cells produced by recombinant DNA technology, the purifying being performed by affinity chromatography and ion chromatography.

Also, the term "final concentrate of recombinant factor VIII" refers to a unlyophilized solution obtained by diluting a recombinant factor VIII concentrate with a basic buffer and a stabilizer added thereto.

The pharmaceutical preparation of recombinant factor VIII lyophilized without albumin according to the present invention comprises arginine (L-arginine), isoleucine (L-isoleucine) and glutamic acid (L-glutamic acid) as a stabilizer for stabilizing the recombinant factor VIII, which is used as a therapeutic preparation of hemophilia.

The arginine preferably has a concentration of 6 to 100 mM, more preferably 6 to 42 mM, before lyophilization.

The isoleucine preferably has a concentration of 3.5 to 50 mM, more preferably 7 to 35 mM, before lyophilization.

The glutamic acid preferably has a concentration of 10 to 100 mM, more preferably 10 to 70 mM, before lyophilization.

Examples of the basic buffer of the final concentrate of recombinant factor VIII of the present invention include an appropriate amount of histidine, and a mixture of NaCl and $CaCl_2$.

It is well known in the art that histidine, NaCl and $CaCl_2$ are commonly used as a buffer of human protein.

The present invention will be explained in more detail with reference to the following examples. However, these are provided only for illustration of the present invention and the present invention is not limited thereto.

EXAMPLE 1

In order to discover a material that stabilizes recombinant factor VIII in place of human blood derived albumin, final concentrate compositions for lyophilization of recombinant factor VIII were prepared using lecithin (phosphatidylcholine), sucrose, glycine, polyvinylpyrrorridone (PVP), and amino acids including arginine, isoleucine and glutamic acid as stabilizers, respectively, and then lyophilized. To evaluate the efficacy of the lyophilized recombinant factor VIII compositions, performance levels of the respective compositions were measured in view of activity, cake appearance and clarity.

Materials and testing devices used are as follows.

L-Arginine-HCl (M.W. 210.7, Sigma)

L-Isoleucine (M.W.131.2, Sigma)

L-Glutamic acid (M.W.169.1, Sigma)

L-Histidine-monohydrate (M.W.209.63, Fluka)

Sucrose (M.W.342.3, Sigma)

Tween 80 (Sigma)

PEG 3350 (M.W.3350, Carbowax)

Human serum albumin (20%, KGC)

Glycine (M.W.75.07, Sigma)

PVP (K30) (M.W. 40000, Fluka)

Phosphatidylcholine (Lecithin, Doosan)

FVIII chromogenic assay kit (Coamatic kit, Chromogenix)

96 well incubator (Sanofi-BMS)

ELISA Reader (Magellan)

Coagulometer

FVIII deficient plasma (DADE BEHRING)

Actin (DADE BEHRING)

$CaCl_2$ (DADE BEHRING)

CA buffer (sodium barbital, DADE BEHRING)

lyophilizer VIRTIS-GENESIS 25XL

Turbidity Meter 2400 (HACH)

Purification of Recombinant Factor

A nutrient solution containing recombinant factor VIII obtained by animal cell culture prepared using recombinant DNA technology was purified by affinity chromatography and primary and secondary ion chromatography to give a purified product, which is referred to as a recombinant factor VIII concentrate.

Production of Pharmaceutical Preparation of Recombinant Factor VIII with Stabilizers Comprising Various Ingredients A basic buffer and a stabilizer for each composition shown in Table. 1 were prepared and a purified recombinant factor VIII concentrate was mixed therewith for dilution, yielding 50 to 125 IU/ml of a final concentrate of recombinant factor VIII. 4 ml of the final concentrate was distributed to each 10 ml vial so that a composition of 200 to 500 IU of the final concentrate was contained in each vial to then be lyophilized.

TABLE 1

| Composition | Basic buffer | Stabilizer |
| --- | --- | --- |
| Experiment 1 (Pharmaceutical preparation of recombinant factor VIII with albumin) | 50 mM Histidine 150 mM NaCl 4 mM $CaCl_2$ | 1% Albumin (HSA) 0.3 mM PEG3350 (0.1%) |
| Experiment 2 (Pharmaceutical preparation of recombinant factor VIII with non-ionic surfactant) | 8.9 mM Histidine 192.5 mM NaCl 2.82 mM $CaCl_2$ | 115.4 mM Sucrose 0.125 mg/mL Tween 80 |
| Experiment 3 | 50 mM Histidine 150 mM NaCl 4 mM $CaCl_2$ | 0.3 mM PEG3350 (0.1%) |
| Experiment 4 | 50 mM Histidine 150 mM NaCl 4 mM $CaCl_2$ | 100 mM Sucrose (100–400 mM test) |

TABLE 1-continued

| Composition | Basic buffer | Stabilizer |
| --- | --- | --- |
| Experiment 5 | 50 mM Histidine 150 mM NaCl 4 mM $CaCl_2$ | 100 mM Sucrose 0.3 mM PEG3350 (1%) |
| Experiment 6 | 50 mM Histidine 150 mM NaCl 4 mM $CaCl_2$ | 400 mM Glycine (50–400 mM test) |
| Experiment 7 | 50 mM Histidine 150 mM NaCl 4 mM $CaCl_2$ | 400 mM Glycine 100 mM Sucrose |
| Experiment 8 | 50 mM Histidine 150 mM NaCl 4 mM $CaCl_2$ | Lecithin (1–6) (0.004–0.16 mg test) 100 mM Sucrose |
| Experiment 9 | 50 mM Histidine 150 mM NaCl 4 mM $CaCl_2$ | 0.5% PVP (0.1–1.4% test) |
| Experiment 10 | 50 mM Histidine 150 mM NaCl 4 mM $CaCl_2$ | 0.5% PVP 100 mM Sucrose |
| Experiment 11 | 50 mM Histidine 150 mM NaCl 4 mM $CaCl_2$ | 0.5% 0PVP 50–400 mM Glycine |
| Experiment 12 | 50 mM Histidine 150 mM NaCl 4 mM $CaCl_2$ | 0.5% PVP 100 mM Sucrose 50 mM Glycine |
| Experiment 13 | 50 mM Histidine 150 mM NaCl 4 mM $CaCl_2$ | 0.5% PVP Lecithin (1–6) |
| Experiment 14 | 50 mM Histidine 150 mM NaCl 4 mM $CaCl_2$ | 0.5% PVP Lecithin (1–6) 100 mM Sucrose |
| Experiment 15 | 50 mM Histidine 150 mM NaCl 4 mM $CaCl_2$ | 6–42 mM L-Arginine 7–35 mM Isoleucine 10–70 mM Glutamic acid |
| Experiment 16 | 50 mM Histidine 150 mM NaCl 4 mM $CaCl_2$ | 5 mM L-Arginine 7 mM Isoleucine 57 mM Glutamic acid |

Lyophilization

The composition for the final concentrate prepared by mixing the purified recombinant factor VIII concentrate with each basic buffer and stabilizer and delivered to each vial was transferred to a lyophilizer (VIRTIS-GENESIS 25XL), followed by blast freezing to −45° C., as shown in FIG. 1, and then held in such a blast-frozen state for 6 hours, to then be turned to a vacuum and further held for 6 hours. Thereafter, the temperature was raised slowly up to −20° C. at a rate of 0.2° C./min over 2 hours (Primary annealing), and then held at an equilibrium state at −20° C. for 80 hours. Then, the temperature was raised slowly up to 25° C. at a rate of 0.1° C./min over 7 hours (Secondary annealing) and then held at that temperature for 3 hours. Thereafter, the temperature was further raised up to 33° C. at a rate of 0.11° C./min over 7 hours and then held at that temperature for 20 hours, thereby achieving lyophilization.

After lyophilization, the respective products were stored at cooling chambers of 2 to 8° C. until they are used. When necessary, the activity, cake appearance and clarity of each product were simultaneously measured.

Evaluation of Experimental Performance

The cake appearance, post-reconstitution clarity and post-reconstitution activity of each pharmaceutical preparation of recombinant factor VIII were measured and the results thereof are listed in Table 2.

The cake appearance was observed visually, the clarity was measured in Nephelometric Turbidity Units(NTU) using an HACH Turbidity Meter 2400 manufactured by Hack Company, USA, and the activity was evaluated by chromogenic assay and clotting assay (APTT). The actual measures of the respective measurement parameters were compared with corresponding data of a control composition with human blood derived albumin as a stabilizer. That is to say, cake appearance, clarity and activity of the pharmaceutical preparation of recombinant factor VIII with albumin (Experiment 1) were assumed as 100%, respectively. The initial activity before lyophilization was 107 IU/ml.

without albumin according to the present invention (Experiment 16) with the pharmaceutical preparation of recombinant factor VIII with albumin (Experiment 1) and

TABLE 2

| Composition | Stabilizer | Cake Appearance | Clarity Actual measure (NTU) | Clarity Relative value (%) | Activity Actual measure (IU/ml) | Activity Relative value (%) |
| --- | --- | --- | --- | --- | --- | --- |
| Experiment 1 (Pharmaceutical preparation of recombinant factor VIII with albumin) | 1% Albumin (HSA) 0.3 mM PEG3350 (0.1%) | 100% | 3.0 | 100% | 102 | 100% |
| Experiment 2 (Pharmaceutical preparation of recombinant factor VIII with non-ionic surfactant) | 115.4 mM Sucrose 0.125 mg/mL Tween80 | 80% | 3.0 | 100% | 86 | 84.3% |
| Experiment 3 | 0.3 mM PEG3350 (0.1%) | 30% | 3.6 | 80% | 77 | 75.5% |
| Experiment 4 | Sucrose 100 mM (100–400 mM test) | 80% | 3.0 | 100% | 81 | 79.4% |
| Experiment 5 | 100 mM Sucrose 0.3 mM PEG3350 (1%) | 30% | 3.0 | 100% | 82 | 80.4% |
| Experiment 6 | 400 mM Glycine (50–400 mM test) | 50% | 3.0 | 100% | 89 | 87.3% |
| Experiment 7 | 400 mM Glycine 100 mM Sucrose | 40% | 3.0 | 100% | 90 | 88.2% |
| Experiment 8 | Lecithin (1–6) (0.004–0.16 mg test) 100 mM Sucrose | 80% | 3.6 | 80% | 90 | 88.2% |
| Experiment 9 | 0.5% PVP (0.1–1.4% test) | 100% | 3.0 | 100% | 76 | 74.5% |
| Experiment 10 | 0.5% PVP 100 mM Sucrose | 50% | 3.0 | 100% | 67 | 65.7% |
| Experiment 11 | PVP 0.5% 50–400 mM Glycine | 40% | 3.0 | 100% | 90 | 88.2% |
| Experiment 12 | 0.5% PVP 100 mM Sucrose 50 mM Glycine | 40% | 3.0 | 100% | 75 | 73.5% |
| Experiment 13 | 0.5% PVP Lecithin (1–6) | 100% | 3.6 | 80% | 91 | 89.2% |
| Experiment 14 | 0.5% PVP Lecithin (1–6) 100 mM Sucrose | 40% | 3.3 | 90% | 86 | 84.3% |
| Experiment 15 | 6–100 mM L-Arginine 3.5–50 mM Isoleucine 10–100 mM Glutamic acid | 100% | 3.0 | 100% | 87–92% | 85.3–90.2% |
| Experiment 16 | 35 mM L-Arginine 7 mM Isoleucine 57 mM Glutamic acid | 100% | 3.0 | 100% | 92 | 90.2% |

As shown in Table 2, assuming that cake appearance, clarity and activity the pharmaceutical preparation of recombinant factor VIII lyophilized with human blood derived albumin as a stabilizer were set as 100%, the recombinant factor VIII composition with a non-ionic surfactant (Experiment 2) was relatively poor in view of cake appearance and activity while exhibiting good clarity. On the other hand, when arginine (L-arginine), isoleucine (L-isoleucine) or glutamic acid (L-glutamic acid) were used as the stabilizer in the present invention, the compositions were good in view of cake appearance, clarity and activity (Experiments 13 and 14).

As evident from the result, the use of lecithin as a stabilizer gave rise to high activity but poor post-reconstitution clarity. Also, sucrose and glycine used as stabilizers achieved relatively high activity but poor cake appearance. Further, polyvinylpyrroridone (PVP) as a stabilizer exhibited relatively good performance in cake appearance but resulted in poor activity.

Figure 2:
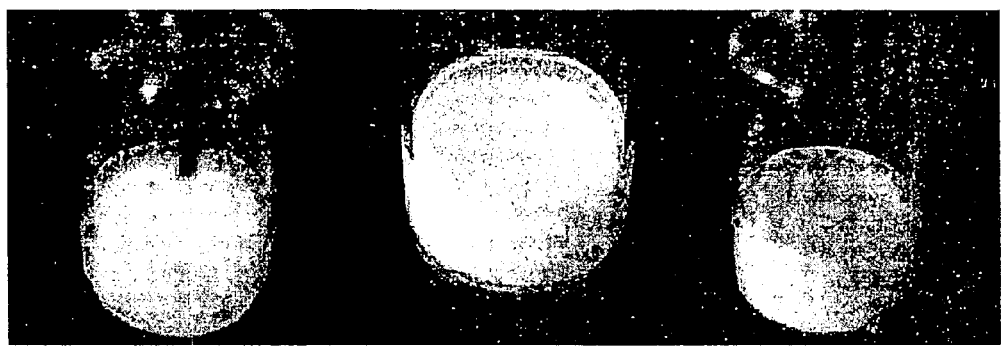
FIG. 2 is a photograph showing the comparison result of a pharmaceutical preparation of recombinant factor VIII without albumin according to the present invention with a pharmaceutical preparation of recombinant factor VIII with albumin and a pharmaceutical preparation of recombinant factor VIII with a non-ionic surfactant.

FIG. 2 is a photograph showing the comparison result of the pharmaceutical preparation of recombinant factor VIII the pharmaceutical preparation of recombinant factor VIII with a non-ionic surfactant (Experiment 2).

Figure 3:
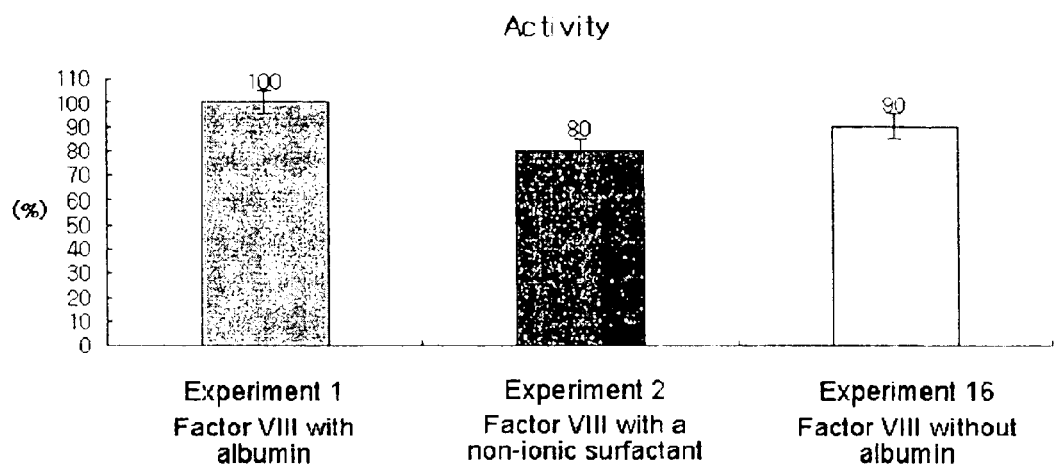
FIG. 3 is a graphical representation for comparing the activity of a pharmaceutical preparation of recombinant factor VIII without albumin according to the present invention with activity levels of a pharmaceutical preparation of recombinant factor VIII with albumin and a pharmaceutical preparation of recombinant factor VIII with a non-ionic surfactant.

FIG. 3 is a graphical representation for comparing the activity of the pharmaceutical preparation of recombinant factor VIII without albumin according to the present invention with activity levels of the pharmaceutical preparation of recombinant factor VIII with albumin (Experiment 1) and the pharmaceutical preparation of recombinant factor VIII with a non-ionic surfactant (Experiment 2). Assuming that the average activity of the recombinant factor VIII composition with albumin was set as 100%, the average activity of the pharmaceutical preparation of recombinant factor VIII with a non-ionic surfactant (Experiment 2) is 80±5% and the recombinant factor VIII composition without albumin according to the present invention was 90±5%, that is, the average activity level of the composition according to the present invention was relatively high.

Figure 4:
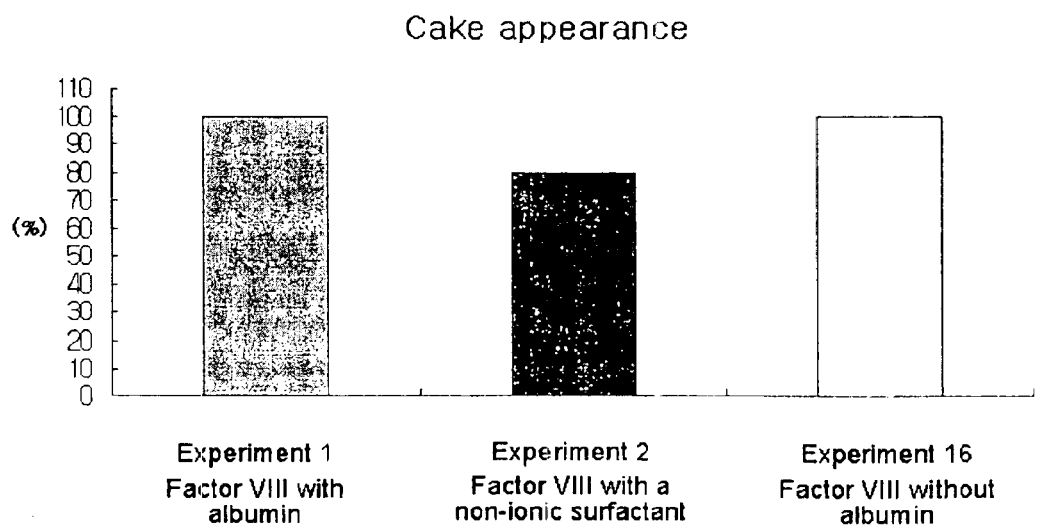
FIG. 4 is a graphical representation for comparing the cake appearance of a pharmaceutical preparation of recombinant factor VIII without albumin according to the present invention with cake appearances of a pharmaceutical preparation of recombinant factor VIII with albumin and pharmaceutical preparation of recombinant factor VIII with a non-ionic surfactant.

FIG. 4 is a graphical representation for comparing the cake appearance of a pharmaceutical preparation of recombinant factor VIII without albumin according to the present invention with cake appearances of the pharmaceutical preparation of recombinant factor VIII with albumin and the pharmaceutical preparation of recombinant factor VIII with a non-ionic surfactant. In detail, assuming that the average cake appearance of the recombinant factor VIII composition with albumin was set as 100%, while the average cake appearance of the recombinant factor VIII composition with a non-ionic surfactant was 80%, the average cake appearance of the recombinant factor VIII composition without albumin according to the present invention was very good, that is, substantially 100%.

Figure 5:
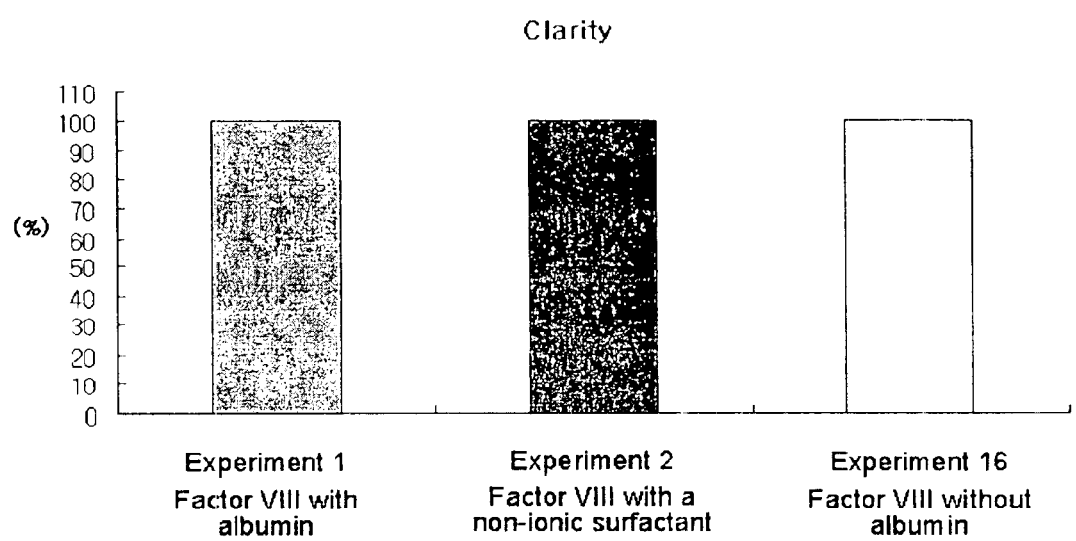
FIG. 5 is a graphical representation for comparing the clarity of the pharmaceutical preparation of recombinant factor VIII without albumin according to the present invention with clarifies of the pharmaceutical preparation of recombinant factor VIII with albumin and pharmaceutical preparation of recombinant factor VIII with a non-ionic surfactant.

FIG. 5 is a graphical representation for comparing the clarity of the pharmaceutical preparation of recombinant factor VIII without albumin according to the present invention with clarity levels of the pharmaceutical preparation of recombinant factor VIII with albumin and pharmaceutical preparation of recombinant factor VIII with a non-ionic surfactant. In detail, assuming that the average clarity of the recombinant factor VIII composition without albumin was set as 100%, the average clarity of the recombinant factor VIII composition with a non-ionic surfactant and the pharmaceutical preparation of recombinant factor VIII without albumin according to the present invention were substantially 100%, that is, there was no difference in clarity between both the pharmaceutical preparations.

EXAMPLE 2

As shown in Example 1, as optimal substitute stabilizers of albumin, the recombinant factor VIII compositions with amino acids including arginine, isoleucine and glutamic acid were lyophilized and optimal conditions of cake appearance were tested, and the results thereof are summarized in Table 3.

glutamic acid, were set at the respective minimum concentrations that allow the formation of cake appearance, that is, 12 mM, 3.5 mM and 19 mM, respectively. In order to study a change in the activity depending on the concentration of each of arginine, isoleucine and glutamic acid, lyophilization was performed to prepare the recombinant factor VIII composition in the same manner as in Example 1 while varying only the concentration of one amino acid with the concentrations of the other amino acids being fixed at the initial concentrations, and chromogenic assay and clotting assay were performed to evaluate the activity performance of the composition. The activity of the recombinant factor VIII composition was indicated as percentile (%) relative to that of the recombinant factor VIII composition with albumin.

Table 4 shows evaluation results of activity levels measured while varying only the concentration of arginine in a range of 6 to 100 mM with the concentrations of isoleucine and glutamic acid being fixed at 3.5 mM and 19 mM, respectively, which are minimum concentrations that allow perfect formation of lyophilized cake. Before lyophilization, the activity was 107 IU/ml.

TABLE 4

| Arginine (mM) | 6 | 12 | 18 | 24 | 30 | 36 | 42 | 48 | 75 | 90 | 100 |
|---|---|---|---|---|---|---|---|---|---|---|---|
| Activity (IU/ml) | 77 | 82 | 83 | 86 | 88 | 92 | 88 | 86 | 81 | 76 | 72 |
| Relative to composition with albumin (Experiment 1) (%) | 75.5% | 80.4% | 81.4% | 84.3% | 86.2% | 90.% | 86.2% | 84.3% | 79.4% | 74.5% | 70.6% |

(Concentrations of isoleucine and glutamic acid being fixed at 3.5 mM and 19 mM, respectively)

As shown in Table 4, the compositions exhibited relatively high activity at various concentrations of arginine over the overall range of 6 to 100 mM. In particular, when the concentration of arginine was 12 to 48 mM, the composition of the present invention exhibited high activity of greater than 80% that of the recombinant factor VIII with albumin. As the concentration of arginine increases, the activity thereof also increases to reach the optimal activity, that is, 90%, when the concentration of arginine was 36 mM.

Table 5 shows evaluation results of activity levels measured while varying only the concentration of glutamic acid in a range of 10 to 100 mM with the concentrations of arginine and isoleucine exhibiting the optimal activity being fixed to 36 mM and 3.5 mM, respectively. Before lyophilization, the activity was 107 IU/ml.

TABLE 3

| Cake appearance | Experiment 17 | Experiment 18 | Experiment 19 | Experiment 20 | Experiment 21 | Experiment 22 | Experiment 23 |
|---|---|---|---|---|---|---|---|
| Arginine (mM) | 6 | 12 | 18 | 24 | 30 | 36 | 42 |
| Isoleucine (mM) | 0 | 4 | 7 | 11 | 14 | 18 | 21 |
| Glutamic acid (mM) | 10 | 19 | 29 | 38 | 48 | 57 | 67 |
| Relative to composition with albumin in Experiment 1 (%) | 60% | 100% | 100% | 100% | 100% | 100% | 60% |

As shown in Table 3, when a composition comprises 12 to 36 mM arginine, 4 to 18 mM isoleucine, and 19 to 57 mM glutamic acid, it exhibited the optimal cake appearance relative to the control composition with albumin.

EXAMPLE 3

Based on the results shown in Table 3, initial concentrations of three amino acids, that is, arginine, isoleucine and

TABLE 5

| Glutamic acid (mM) | 10 | 19 | 29 | 38 | 48 | 57 | 67 | 76 | 86 | 95 | 100 |
|---|---|---|---|---|---|---|---|---|---|---|---|
| Activity (IU/ml) | 79 | 79 | 82 | 84 | 88 | 92 | 88 | 82 | 78 | 76 | 67 |
| Relative to composition with albumin (Experiment 1) (%) | 77.5% | 77.5% | 80.4% | 82.4% | 86.3% | 90.2% | 86.3% | 87.1% | 76.5% | 74.5% | 65.7% |

(Concentrations of arginine and isoleucine being fixed at 36 mM and 3.5 mM, respectively)

As shown in Table 5, the compositions exhibited relatively high activity at various concentrations of glutamic acid over the overall range of 10 to 100 mM. In particular, when the concentration of glutamic acid was 29 to 76 mM, the composition of the present invention exhibited relatively high activity of greater than 80% that of the recombinant factor VIII with albumin. As the concentration of glutamic acid increases, the activity of the composition also increases to reach the optimal activity, that is, 90%, when the concentration of glutamic acid was 57 mM.

Table 6 shows evaluation results of activity levels measured while varying only the concentration of isoleucine in a range of 10 to 50 mM with the concentrations of arginine and glutamic acid exhibiting the optimal activity being fixed to 36 mM and 57 mM, respectively. Before lyophilization, the activity was 107 IU/ml.

TABLE 6

| Isoleucine (mM) | 0 | 4 | 7 | 11 | 14 | 18 | 21 | 25 | 50 |
|---|---|---|---|---|---|---|---|---|---|
| Activity (IU/ml) | 81 | 82 | 92 | 86 | 86 | 82 | 73 | 67 | 62 |
| With albumin (Experiment 1) | 79.4% | 80.4% | 90.2% | 84.3% | 84.3% | 80.4% | 71.6% | 65.7% | 60.8% |

(Concentrations of arginine and glutamic acid being fixed at 36 mM and 57 mM, respectively)

As shown in Table 6, the compositions exhibited relatively high activity at various concentrations of glutamic acid over the overall range of 0 to 50 mM. In particular, when the concentration of glutamic acid was 0 to 18 mM, the composition of the present invention exhibited relatively high activity. When the concentration of glutamic acid was 7 mM, the composition exhibited the optimal activity.

Experiments were carried out to examine optimal conditions required for maintaining the activity for an amino acid stabilizer, instead of albumin. The experimental results showed that, compared to the control composition with albumin, the optimal conditions were exhibited when concentrations of arginine, isoleucine and glutamic acid were 36 mM, 7 mM and 57 mM, respectively. To evaluate the efficacy of the lyophilized recombinant factor VIII compositions, performance levels of the respective compositions were measured in view of activity, cake appearance and clarity.

According to the present invention, the pharmaceutical preparation of recombinant factor VIII lyophilized with a particular amino acid, rather than albumin, as a stabilizer, exhibits substantially the same efficacy as in the case where albumin is used as a stabilizer, in view of activity, cake appearance and clarity, while causing few side effects in human. In view of activity and cake appearance, the pharmaceutical preparation of recombinant factor VIII lyophilized with a particular amino acid according to the present invention is also relatively good and is better than the pharmaceutical preparation of recombinant factor VIII with a non-ionic surfactant.

What is claimed is:

1. A pharmaceutical preparation of recombinant factor VIII lyophilized with a stabilizer comprising arginine, isoleucine and glutamic acid, the stabilizer stabilizing the recombinant factor VIII, which is used as a therapeutic preparation of hemophilia.

2. The pharmaceutical preparation of claim 1, wherein before lyophilization, the arginine has a concentration of 6 to 100 mM.

3. The pharmaceutical preparation of claim 1, wherein before lyophilization, the arginine has a concentration of 6 to 42 mM.

4. The pharmaceutical preparation of claim 1 or 2, wherein before lyophilization, the isoleucine has a concentration of 3.5 to 50 mM.

5. The pharmaceutical preparation of claim 1 or 2, wherein before lyophilization, the isoleucine has a concentration of 7 to 35 mM.

6. The pharmaceutical preparation of claim 1 or 2, wherein before lyophilization, the glutamic acid has a concentration of 10 to 100 mM.

7. The pharmaceutical preparation of claim 1 or 2, wherein before lyophilization, the glutamic acid has a concentration of 10 to 70 mM.

8. The pharmaceutical preparation of claim 1, wherein before lyophilization, the arginine has a concentration of 6 to 42 mM, the isoleucine has a concentration of 7 to 35 mM and the glutamic acid has a concentration of 10 to 70 mM.

* * * * *